United States Patent
Carmignani et al.

(10) Patent No.: US 6,524,447 B1
(45) Date of Patent: Feb. 25, 2003

(54) APPARATUS AND METHOD FOR PHOTOCATALYTIC PURIFICATION AND DISINFECTION OF WATER AND ULTRAPURE WATER

(75) Inventors: Gary M. Carmignani, Occidental, CA (US); Lee W. Frederick, Santa Rosa, CA (US)

(73) Assignee: Titan Technologies, Santa Rosa, CA (US)

( * ) Notice: Subject to any disclaimer, the term of this patent is extended or adjusted under 35 U.S.C. 154(b) by 0 days.

(21) Appl. No.: 09/721,803

(22) Filed: Nov. 22, 2000

Related U.S. Application Data

(60) Provisional application No. 60/166,855, filed on Nov. 22, 1999.

(51) Int. Cl.[7] .............................. C07B 63/00; C07C 1/00; B01D 53/00; B01J 19/12; C02F 1/48
(52) U.S. Cl. ............................. 204/158.2; 204/157.15; 204/157.3; 588/222; 422/186.3; 210/748
(58) Field of Search ................. 204/157.15, 157.3, 204/158.2; 588/222; 250/492.2; 422/186, 186.3; 210/748

(56) References Cited

U.S. PATENT DOCUMENTS

| | | | |
|---|---|---|---|
| 4,863,608 A | 9/1989 | Kawai et al. | 210/638 |
| 4,966,759 A | 10/1990 | Robertson et al. | 422/186 |
| 5,069,885 A | 12/1991 | Ritchie | 422/186 |
| 5,126,111 A | 6/1992 | Al-Ekabi et al. | 422/186.3 |
| 5,256,616 A | 10/1993 | Heller et al. | 502/350 |
| 5,302,356 A | 4/1994 | Shadman et al. | 422/186.3 |
| 5,308,454 A * | 5/1994 | Anderson | 204/59 R |
| 5,395,522 A | 3/1995 | Melanson | 210/202 |
| 5,501,801 A | 3/1996 | Zhang et al. | 210/748 |
| 5,637,231 A | 6/1997 | Hill et al. | 210/748 |
| 5,736,055 A | 4/1998 | Cooper | 210/748 |
| 5,766,455 A * | 6/1998 | Berman et al. | 210/199 |
| 5,790,934 A | 8/1998 | Say et al. | 422/186 |
| 5,868,924 A | 2/1999 | Nachtman et al. | 210/85 |
| 5,919,422 A | 7/1999 | Yamanaka et al. | 422/121 |
| 6,030,526 A | 2/2000 | Porter | 210/198.1 |
| 6,054,227 A | 4/2000 | Greenberg et al. | 428/701 |
| 6,066,359 A | 5/2000 | Yao et al. | 427/126.3 |
| 6,117,337 A | 9/2000 | Gonzalez-Martin et al. | 210/748 |
| 6,135,838 A | 10/2000 | Wang | 445/22 |
| 6,136,816 A | 10/2000 | Gonzalez-Martin et al. | 210/198.1 |
| 6,241,856 B1 | 6/2001 | Newman et al. | 204/157.3 |
| 6,306,796 B1 | 10/2001 | Suzue et al. | 502/350 |
| 6,340,711 B1 | 1/2002 | Ohmori et al. | 516/79 |
| 2001/0003358 A1 | 6/2001 | Terase et al. | 252/62 |
| 2002/0006866 A1 | 1/2002 | Ohmori et al. | 502/350 |
| 2002/0023800 A1 | 2/2002 | Ohmori et al. | 181/294 |

OTHER PUBLICATIONS

Suvorov et al., "Oxidation of Organic Compounds. C. Vanadium Pentoxide–Titanium Dioxide Catalyst for Oxidation and Oxidative Ammonolysis of Organic Compounds", Vestn. Akad. Nauk. Kaz SSR, vol. 10, PP. 16–23. (no month available) 1974.*

* cited by examiner

*Primary Examiner*—Edna Wong
(74) *Attorney, Agent, or Firm*—Crowell & Moring LLP

(57) ABSTRACT

An apparatus and method for the photocatalytic purification and ultrapurification of water. Water containing organic, inorganic and/or biological contaminants is directed through an open cell, three dimensionally reticulated, fluid permeable, semiconductor unit. Within the unit, a semiconductor surface capable of promoting electrons from its valence band to its conduction band, when exposed to a photoactivating light source, removes the contaminants through a photocatalytic reaction.

58 Claims, 6 Drawing Sheets

APPARATUS AND METHOD FOR PHOTOCATALYTIC PURIFICATION AND DISINFECTION OF WATER AND ULTRAPURE WATER

This application claims priority from Provisional Application # 60/166,855 filed Nov. 22, 1999.

FIELD OF THE INVENTION

The present invention generally relates to a method and apparatus for the purification and disinfection of water. More specifically, the present invention relates to an apparatus and method of use of a semiconductor material for the photocatalytic degradation of organic and inorganic pollutants and microorganisms in water and ultrapure water[1]. The present invention is an apparatus and method incorporating a rigid, open cell, three dimensionally reticulated, fluid permeable, photocatalytic semiconductor unit.

[1] Ultrapure water as used herein refers to water that is pretreated by methods know to those skilled in the art to remove suspended and dissolved inorganic and organic mater from municipal, well water and any other water source.

BACKGROUND OF THE INVENTION

Heterogeneous photocatalysis is the general term that describes the technical approach, [Mills, A.; Le Hunte, S.; "An Overview of Semiconductor Photocatalysis," J. Photo-Chem. & PhotoBio. A: Chemistry 108 (1997) 1–35] and [Hoffman, M. R.; Martin, S. T.; Choi, W.; Bahnemann, D. W.; "Environmental Applications of Semiconductor Photocatalysis," Chem Rev 1995, 95, 69–96]. The specific process is properly described as semiconductor-sensitized photomineralization of organics by oxygen. It may be summarized as:

Organic pollutant+$O_2$ ⇒ $CO_2$+$H_2O$+mineral acid $hv > E_{bg}$ where hv represents the energy of a photon and $E_{bg}$ is the bandgap energy separating electrons in the valence band of the semiconductor from those in its conduction band.

The process is driven by photons having more energy than the bandgap of the semiconductor they irradiate. Each such photon absorbed by the semiconductor will promote an electron from the valence band producing a conduction band electron (e−) and a valence band hole (h+). When the resultant electron-hole pair migrates to the semiconductor/solution interface, oxidation-reduction processes are initiated. These include:

Holes:

Acidic or neutral solutions: $H_2O + h^+ \Rightarrow OH\cdot + H^+$

Alkaline solutions: $OH^- + h^+ \Rightarrow OH\cdot$

Electrons:
Uncertain reaction pathway resulting in the reduction of oxygen to various reactive species including $O\cdot$, $O_2\cdot$, $O_2H\cdot$, $HO_2^-$, $H_2O_2$ and $OH\cdot$.

Of particular importance is the formation of OH·, the hydroxyl radical. The hydroxyl radical is an extremely potent oxidizing agent (redox potential of +2.8 V), capable of oxidizing almost all organic compounds. By comparison, the redox potentials for the more conventional oxidants chlorine and ozone are +1.36 and +2.07 V, respectively. Hydroxyl radicals also kill and breakdown microorganisms. The reactive species created by the reduction of oxygen will also oxidize organic compounds. All active species are created from water, and decay back to water. Light is the only reagent required.

Semiconductor photocatalysts that have been demonstrated for the destruction of organic contaminants in fluid media include but are not limited to: $TiO_2$, ZnO, $CaTiO_3$, $SnO_2$, $MoO_3$, $Fe_2O_3$, and $WO_3$. TiO2 is the most widely investigated because it is chemically stable, has a suitable bandgap structure for UV/Visible photoactivation, and is relatively inexpensive.

$TiO_2$ exists in two principal crystalline forms: rutile and anatase. The rutile form of TiO2 is widely used as a pigment and can be found in almost anything white—paint, paper, textiles, inks, plastics and cosmetics. Anatase, the low temperature form (stable below ~600° C.) is the most photoactive form. Nanoscale (5–50 nm) anatase particles with very high surface areas (50–500 m²/gm) show high photoactivity when irradiated with UV light (<390 nm) in the presence of water.

The deposition of a transition metal (e.g., platinum, palladium, silver) on the surface of the anatase increases the photocatalytic activity by approximately a factor of two. A variety of methods improve the quantum efficiency of $TiO_2$ by doping with various metals to extend the spectral response into the more efficient visible light wavelengths, [Borgarello, E. et al. "Visible Light Induced Water Cleavage in Colloidal Solutions of Chromium-Doped TiO2 Particles," J. Am. Chem. Soc. 1982, 104, 2996–3002] or to increase the minority carrier diffusion length, [Augustynski, J.; Hinden, J. Stalder, C.; J. Electrochem. Soc. 1977, 124, 1063] or achieve efficient charge separation to increase carrier lifetimes, Vogel, R.; Hoyer, P; Weller, H.; "Quantum-Sized PbS, CdS, Ag2S, Sb2S3 and Bi2S3 Particles as Sensitizers for Various Nanoporous Wide-Bandgap Semiconductors," J. Phys. Chem. 1994, 98, 3181–3188].

Most of the early research on semiconductor photocatalysis concerned methods using titanium dioxide (TiO2) slurries or TiO2 wash coatings onto or inside a glass tube and the photodegradation of organic compounds and their intermediates in water. These methods of using TiO2 have limitations for commercial applications. For example, although TiO2 slurry has tremendous surface area and has acceptable quantum yields, there are serious limitations to the removal of the TiO2 particles from the purified water. While wash coating TiO2 onto glass avoids the removal limitations of the slurry approach, it has its own problems in that insufficient surface area is presented for effective destruction of organics within a reasonable time period. Additionally, the wash coat is not firmly attached to the glass resulting in a loss of TiO2 to the water stream and a concomitant reduction in photocatalytic activity.

Kraeutler and Bard made a photocatalytic reactor of water slurry of suspended TiO2 powder, in the anatase crystalline form, and studied the decomposition of saturated carboxylic acid, [J. ACS 100 (1978) 5985–5992]. Other researchers used UV-illuminated slurries of TiO2 for the photocatalyzed degradation kinetics of organic pollutants in water.

Mathews created a thin film reactor by wash coating TiO2, (Degussa P25™), particles to the inside of a 7 millimeter long borosilicate glass tube wound into a 65-turn spiral. The reactor was illuminated with a 20 watt, black light UV fluorescent tube. He monitored the destruction of: salicylic acid, phenol, 2-chlorophenol, 4-chlorophenol, benzoic acid, 2-naphthol, naphthalene, and florescin in water, [J. Physical Chemistry 91 (1987) 3328–3333].

As an improvement over the prior art approaches, U.S. Pat. No. 4,892,712 to Robertson et al. disclosed the attachment by the sol-gel process of anatase TiO2 to a fiberglass mesh substrate. This mesh was wrapped around a light source contained within a quartz glass cylinder and emitting UV radiation in a wavelength range of 340 to 350 nanometers (nm). The entire structure was placed within a stainless steel cylinder containing fluid inlet and outlet ports thereby creating a reactor. Polluted water was passed through this reactor for purification. Unlike the present invention, Robertson's mesh is not rigid, open cell, three dimensionally reticulated and lacks permanent bonding of the semiconductor to the mesh.

Professor I. R. Bellobono prepared photocatalytic membranes immobilizing 23% of Titanium Dioxide (Degussa P-25). Controlled amounts of appropriate monomers and polymers, containing the semiconductor to be immobilized and photoinitiated by a proprietary photocatalytic system was photografted onto a non-woven polyester tissue. The final porosity of the photosynthesized membrane was regulated at 2.5–4.0 microns. He trade named this membrane "Photoperm"™. A fluid containment structure surrounded the membrane creating a reactor. The reactor volume occupied by the fluid was 2.5 liters (l) and the membrane surface area was 250 square centimeters ($cm^2$). The reactor was illuminated with a cylindrical high-pressure mercury arc lamp at a power of 2 kilowatts (kW) and at a wavelength of 254 nm. Water flowed into the center of the reactor and moved out tangential to the lamp through the membrane. This system was used to destroy phenol in water, ["Effective Membrane Processes. New Perspectives" (R. Paterson, ed.) BHR, Mech. Eng. Publ., London (1993), pg 257–274]. The process was patented in Italy in 1995, Italian Pat. No. IT1252586. Unlike the present invention, Bellobono's apparatus is not inert, not open cell, not three dimensionally reticulated and not durable.

Cittenden, et al. discloses a method and apparatus for destroying organic compounds in fluids [The 1995 American Society of Mechanical Engineers (ASME) International Solar Energy Conference, Maui, Hawaii, USA]. TiO2 was attached by wash coating to a 35×60-mesh silica gel substrate. The substrate was placed within a plastic tube that allowed the penetration of UV light. Organic pollutants in a water stream passed axially through the tube. Natural light and/or artificial UV light oxidize the investigated organic pollutants. Unlike the present invention, Cittenden's invention is not open cell, not three dimensionally reticulated, not durable, and has very limited fluid permeability.

Anderson discloses a method to make ceramic titanium membranes by the sol-gel process. [J. Membrane Science 30 (1988) 243–258]. These membranes are porous and transparent to UV illumination. They are made from a titanium alkoxide and then fired to form the anatase crystalline structure. Unlike the present invention, Anderson's invention is not open cell, not three dimensionally reticulated, not durable, and has very limited fluid permeability.

Thus, while attempts were made in the prior art to enhance quantum yields by increasing semiconductor surface area and improving UV light penetration, serious limitations remain to the commercial development of an efficient, durable photocatalytic purification apparatus and method for its use. In Robertson, in addition to the severe limitations already above noted, the flexible strands of fiberglass precluded the permanent attachment of TiO2 because, as water passed by, the fiberglass strands bent and flexed releasing TiO2 particles, particularly at high fluid flow rates. For Bellobono, in addition to all the limitations also above noted, the photocatalytic process gradually oxidized the organic membrane reducing its activity over time.

In addition to all the limitations also above noted, Cittenden's TiO2 sloughed-off because it was wash coated to the silica gel substrate. In addition, the void space between silica particles was so small that flow through the system was restricted making the structure unsuitable for commercial applications. In Andersen's membrane, in addition to the limitations above noted, limitations on the structural integrity of these membranes exist particularly at high fluid velocities needed for efficient industrial applications.

SUMMARY OF THE INVENTION

The object of the present invention is to substantially improve upon the prior art to produce an effective, quantum efficient, durable, economic, commercial apparatus for the rapid photocatalytic purification and disinfection of water and ultrapure water. At the present time in the semiconductor processing industry, current technology struggles to achieve 2 parts-per-billion (ppb) in Total Organic Carbon (TOC). This represents a limit on the industry's ability to achieve further improvements in the chip density and speed. The present invention, which achieves 500 parts-per-trillion (ppt) in TOC, or better, represents a breakthrough for both the water purification and semiconductor industry. The invention also has profound implications for other water purification systems, including those related to environmental cleanup.

The apparatus of the present invention involves a reactor apparatus and a method for its use for photopromoted, catalyzed degradation of compounds in a fluid stream. The effectiveness of the process is determined in part by the mass transfer efficiency, which is the rate at which the contaminant is transported from the fluid stream to the photocatalytic surface where it can be destroyed. Mass transfer is greatly aided by proximity. Thus, it is desirable, to the greatest degree possible, to have the catalyst uniformly distributed in the volume of water to be treated, such that a contaminant is never far from a catalyst surface.

Another consideration is the uniform illumination of the catalyst within the volume of water to be treated. Since the catalyst itself absorbs the light, its concentration in the volume should be limited to allow sufficient penetration of the activating photons. In addition, the support structure should not block illumination of the volume of water to be treated. Thus, the volume fraction of support material should be minimized and/or it should have high transparency to the activating photons. To enhance volumetric illumination, in an embodiment which employs a substrate, the substrate material is preferably made from glass or other materials transparent or semitransparent to the photoactivating wavelengths. This is possible using three dimensionally reticulated photocatalytic semiconductor unit. In an embodiment which bonds or chemically integrates the substrate with the semiconductor, the unit is also preferably made from transparent or semitransparent materials.

The water flow through the catalyst should be turbulent to improve mixing and mass transfer rates between the organic contaminants and the oxidizing species generated at the catalyst surface. Laminar flow should be avoided.

The reticulated structure utilized in the present invention substantially represents a breakthrough over the prior art and allows for the commercial use of photocatalytic technology in ultrapure water production because it optimizes mass transfer, surface area, illumination, water flow, durability, rigidity, etc. The photocatalytic semiconductor unit provides a high surface area, rigid structure to which the photocatalyst is adhered or incorporate. The interstitial struts forming the open celled structure of the photocatalytic semiconductor unit are relatively thin, so volume fraction of substrate support material is low and flow is not significantly restricted. The ramification and alignment of the struts with respect to the flow direction will generate tortuous flow paths and enhanced mass transport. The rigidity of the support structure provides a stable base to permanently attach or incorporate a highly active $TiO_2$ surface.

DETAILED DESCRIPTION OF PREFERRED EMBODIMENT

Figure 1A:
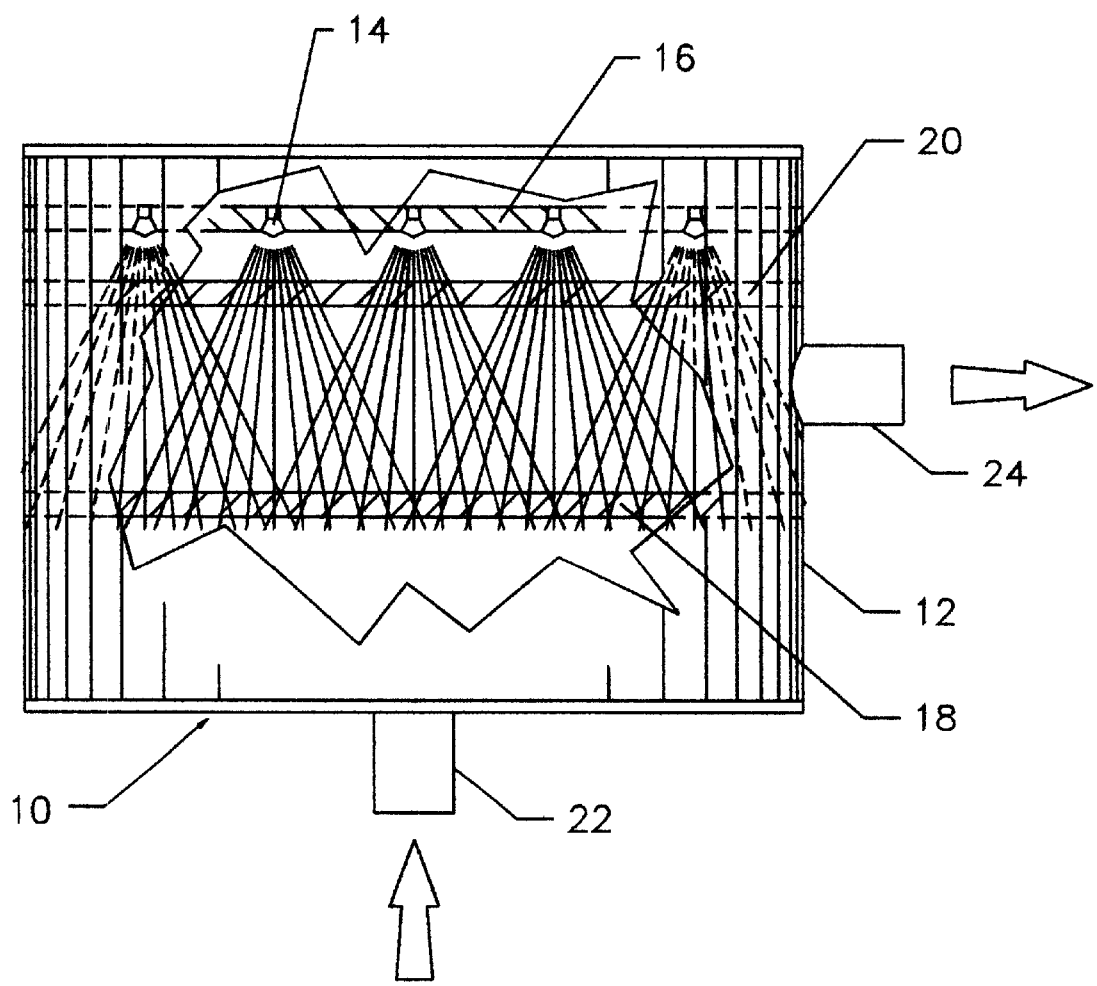
FIG. 1A shows a point of use reactor with LED's as the source of photoactivating light.

The present invention is directed to the use of the three dimensionally reticulated photocatalytic semiconductor unit photo-actively charged with a semiconductor for use in a reactor apparatus and method for the purification and disinfection of water for the semiconductor industry, environmental cleanup, and for the home point-of-use market.

In a preferred embodiment, the present invention discloses an apparatus and method for purifying water and ultrapure water that solves problems of the prior art by presenting to a fluid, a rigid, three dimensionally reticulated, open-cell material characterized by an inert, porous, photo-activating light semitransparent, fluid permeable, high surface area substrate onto which a photocatalytic semiconductor layer is permanently bonded or into which it is incorporated. The material described in the present invention and the apparatus and method for its use in photocatalytic purification and disinfection of water and ultrapure water is further characterized by high contact efficiency turbulent fluid flow with relatively low pressure drop.

Of course these are just examples and one familiar with the art recognizes that the current invention can be used to purify water in manufacturing semiconductors and pharmaceuticals, in biotechnology, power plant water, bottled water, municipal water supplies, point of use, just to mention a few.

Although never before used for the present purpose, three dimensionally reticulated, open-cell substrates made from a variety of materials are scientifically described and commercially available. Such materials include alumina, titania, aluminum, gold, copper, metal alloys, carbon, silica, glass, quartz, organic polymers, silicon carbide, silicon nitride, boron nitride, tungsten carbide, and many more. One of many methods of making reticulated substrate is described in the prior art—U.S. Pat. No. 3,052,967 to Fischer; U.S. Pat. No. 3,946,039 to Walz; U.S. Pat. No. 4,568,595 to Morris; and U.S. Pat. No. 5,441,919 to Park et al. Substrates may also be made utilizing the stereolitograhic process or selective laser sintering or other methods familiar to those experienced in the art. The rigid three dimensionally reticulated substrate utilized in the current invention possesses a highly variable surface, with an easily controlled surface roughness and a huge macro surface area, depending on the overall pore size from 10 to 200 ppi. The concentrated yet compact surface area opens the possibility of using a great variety of attachment methods; such as, without being limited to, sol-gel process, ion assisted gun deposition ion beam sputtering, chemical vapor deposition, aerosol application, evaporation deposition, etc.

Literature and the prior art explain the procedures necessary for permanent bonding of TiO2 to a substrate. For example for sol-gel process refer to: U.S. Pat. No. 4,892,712 to Robertson; U.S. Pat. No. 6,013,372 to Hayakawa, et al., and U.S. Pat. No. 6,093,676 to Heller, et al., or in literature, Preparation, Microstructure and Photocatalytic Activity of Porous TiO2 Anatase Coatings by sol-gel Processing, [J Sol-Gel Science and Technology 17 (2000) 163–171] by Jiaguo Yu, et al; Nanocrystallite Titanium Dioxide Films Made by the Sol-Gel Method Using Reverse Micelles, [J Sol-Gel Science and Technology 10 (1997) 83–89] by E. Stathaios, et al. For chemical vapor refer to: U.S. Pat. No. 5,389,401 to Gordon, or in Metal Organic CVD of Nanostructured Composite TiO2-Pt Thin Films: A Kinetic Approach, [Chem. Vapor Deposition 5 (1999) 13–20] by Giovanni, et al. Yet another method condenses from aerosolized semiconductor droplets, as described in Deposition of Multifunctional Titania Films by Aerosol Routes, [J. Am. Ceramic Soc. 82 (1999) 10] by G. Yang and Pratim Biswas. While these are some of the popular methods for attaching semiconductor films, we do not limit ourselves to variations on them and other methods that are to be found in prior art.

In another embodiment the semiconductor layer is chemically formed in situ by oxidation of the underlying metal, either electrochemically or thermally or by chemical reaction. See for example Titanium Dioxide Film Electrodes Prepared by Thermal Oxidation, [J. Electrochem. Soc. 139, no. 7, (1992) 1803 by Choi Yong-kook et. al. and In Situ Raman Spectra of Anodically Formed Titanium Dioxide Layers in Solutions of H2SO4, KOH and HNO3, [J. Electrochem. Soc. 138 no. 10 (1991) 2964].

In a further embodiment the substrate is made of the same material as the semiconductor layer and the two materials are chemically integrated. This creates stable surface capable of withstanding tremendous turbulent flow.

Photocatalytic activity of many semiconductor surfaces is enhanced by a process of doping or coating these surfaces with a variety of metals, including transition metals such as, but not limited to, platinum, palladium, ruthenium, iridium, rhodium, gold, silver, copper, tin, iron, cobalt, vanadium, niobium, and zinc. Combinations of these metals and their oxides, sulfides or other compounds are known to those experienced in these arts. By altering the doping of TiO2 the band gap energy can be shifted to the visible spectrum (400 nm–700 nm). Zang. et al. showed that the addition of platinum (IV) halide shifted the band gap energy required for TiO2 form 335 nm to 366 mn to 400 nm into the visible spectrum. [Amorphous Microporous Titania Modified Platinum (IV) Chloride—A New Type of Hybrid Photocatalyst for Visible Light Detoxification. J Phys. Chem. B 102 (1998) 10765–10771]. Doping with iron or chromium produces similar results. [Visible Light Induced Water Cleavage in Colloidal Solutions of Chromium-doped Titanium Dioxide Particles. JACS 104 (1982) 2996–3002, by E. Borgarello, et al.]

An enhancement of the preferred embodiment is a film made from the anatase form of TiO2 in a usable grain size for particles from 1 to 30 nanometers in diameter. An active surface thickness can vary from 1 to 190 micrometers. Platinum was found to be effective dopant to increase activity when applied in the range of from 0.5 to 3% by weight of the titanium dioxide. Platinum as specified above increased the TOC destruction activity by a factor of 2 to 3. A further enhancement of the dopant is a vanadium compound, such as vanadium pentoxide (7% by weight of the TiO2) on a semiconductor such as TiO2, when used in combination with ozone. It increases the rate of destruction of TOC by a factor of 2–8 times. This enhancement applies in the dark as well as under illumination. This means that if light does not penetrate to the interior of the substrate, TOC will still be destroyed.

A further enhancement of the embodiments of the apparatus and method of the present invention consists of the use of a combination or set of reticulated substrates, each with its own particular variety of parameters and enhancements. Each member of the set may be designed to operate on a particular component of the TOC, such as, but not limited to, polar/non-polar components, hydrophobic/hydrophilic components, aromatic/aliphatic components, alcoholic/acidic components and chemical/biological components. The members of the set are used in a series combination where water flows thru first one member and then another member. This enhancement enlarges the scope of the invention by bringing a complete collection of destruction capabilities to bear on combinations of contaminants, even though individual members of the set are alone incapable of achieving acceptable overall TOC destruction levels.

Preferred light sources include, without being limited to low, medium and high-pressure mercury lamps and ultraviolet emitting LED's, or any other light source that activates the semiconductor.

Drawing attention to existing U.S. Pat. No. 5,116,582, to Cooper, et al. entitled Photocatalytic Slurry Reactor Having Turbulence Generating Means, the creation of turbulence has been recognized in prior art as a necessary condition for effective TOC destruction. The connection is the need for organic molecules present in the water being purified to come into close proximity to the active surface before they can be destroyed. The reticulated photocatalytic semiconductor unit described for use in the apparatus and method of the present invention behaves superbly in this regard in that it causes water flowing through its pores to shear, thrashing from side to side within the pores, and to speed up and slow down according to the cross section of the pore openings, creating extreme turbulence within the pore structures themselves (microturbulence). Reticulated photocatalytic semiconductor units provide many ways to control turbulence by controlling pores sizes and pore distributions, pore wall formations and surface roughnesses.

As a further enhancement of the invention, known methods exist to grade the size of the pores so that they start large near the surface at approximately 10 ppi and then diminish in size towards the photocatalytic semiconductor unit's interior at approximately 200 ppi, thus providing tailored light guides. Additionally, the water itself may be modified such as by adding microscopic gas bubbles, to guide the light into the interior. The materials of construction of the photocatalytic semiconductor unit can be varied from reflective (metals) to opaque (TiO2, carbon, metals) to transparent (silica, alumina) to provide further control over the penetration of the photoactivating light. Innovative designs can incorporate light guides such as, but not limited to, light fibers, quartz blocks, voids, gaps and separations.

Although particular embodiments of the present invention have been described and illustrated herein, it should be recognized that modifications and variations might readily occur to those skilled in the art and that such modifications and variations may be made without departing from the spirit and scope of our invention. Consequently, our invention as claimed may be practiced otherwise than as specifically described.

FIG. 1A shows an example of a point of use reactor 10 with LED's as the photoactivating light. Contaminated source water flows into the reactor through inlet 22. The water flows through the reticulated semiconductor unit 18 that is photoactivated by LED lights 14. A support/wiring plate 16 holds the LED lights. A quartz plate 20 is provided to isolate the LED lights from the water flow. Purified water exits the reactor through outlet 24. The point of use reactor enclosure 12 can be constructed from a variety of thermoplastics (polyproplylene, etc), or metals (304 stainless steel, 316 stainless steel, etc), or other materials that are both inert to degradation by the LED light source and resistant to corrosion by water.

The point of use reactor can use a reticulated semiconductor unit that is photoactivated by LED's that emit UV energy at 370 nm or lower. The point of use reactor can also use a reticulated semiconductor unit that is doped to shift the band gap to visible wavelengths. In this reactor, an LED that emits visible wavelengths is utilized. This latter configuration enables a more efficient use of the LED energy.

The point of use reactor is designed to be commercialized into markets defined by low and intermittent demand for purified water, such as potable water in the home. This reactor is superior to existing technologies because it uses only a small percentage of energy and it does not transmit heat to the product water while not in use (eliminating the need to rinse the system to ambient temperature prior to using product water). In addition, the reactor only requires low power electrical energy per LED, making it both safe for the user in an environment that includes water and electricity and enabling the reactor to be utilized in portable applications (battery powered).

Figure 1B:
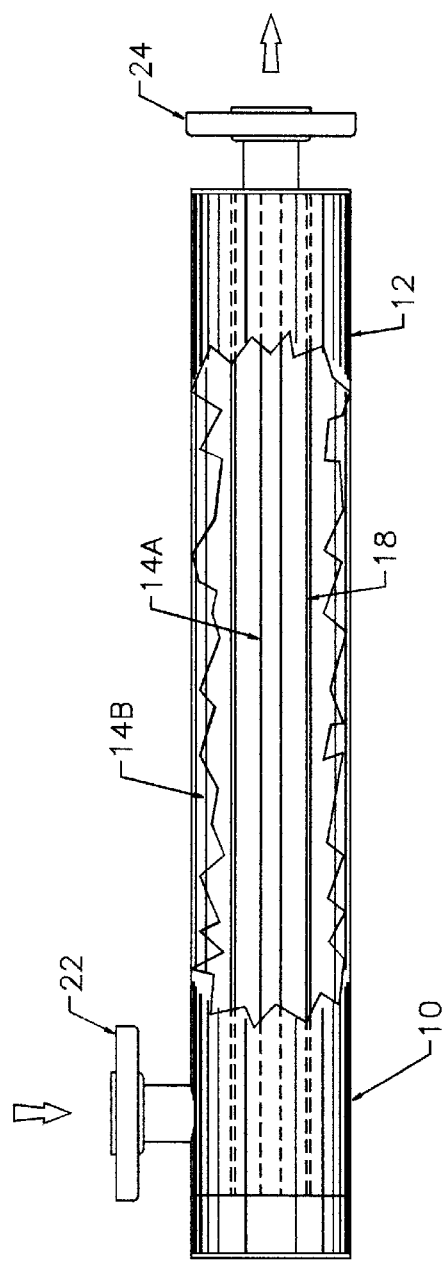
FIG. 1B and FIG. 1C show a cylindrical tube reactor where the water flows in and passes radially through the reticulated photocatalytic substrate and axially past the UV light source.
Figure 1C:
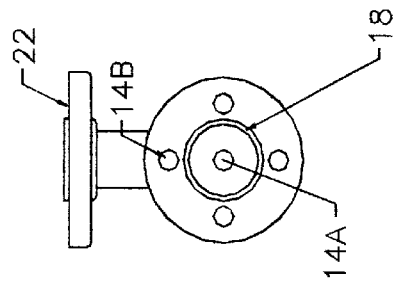

FIG. 1B shows an example of a side view of a commercial/industrial reactor 10 with tube type lamps as the photoactivating light. FIG. 1C is an end view of the same commercial/industrial reactor 10. The reticulated photocatalytic semiconductor unit 18 is a cylinder. Both the exterior photoactivating lights 14B and interior photactivating lights 14A are tubes enclosed by cylindrical quartz sleeves. Contaminated source water flows into the reactor through inlet 22. The contaminated water flows radially through the reticulated semiconductor unit and passes by the exterior photoactivating lights. The contaminated water flows axially through the reactor, where it is purified by both the exterior photoactivating lights and by the interior photoactivating lights. Purified water flows out through outlet 24.

The commercial/industrial reactor 10 is designed to be commercialized into markets defined by high and continuous demand for purified water. The configuration of the reactor is designed to be modular so that longer and/or parallel reactors can be employed for higher flows. Series reactors with different sets of reticulated photocatalytic semiconductor unit specifications and/or different wavelengths for the exterior and interior photoactivating lights can be employed for custom purification of source water with different polar/non-polar components, hydrophobic/hydrophilic components, aromatic/aliphatic components, alcoholic/acidic components, and chemical/biological components.

Figure 2:
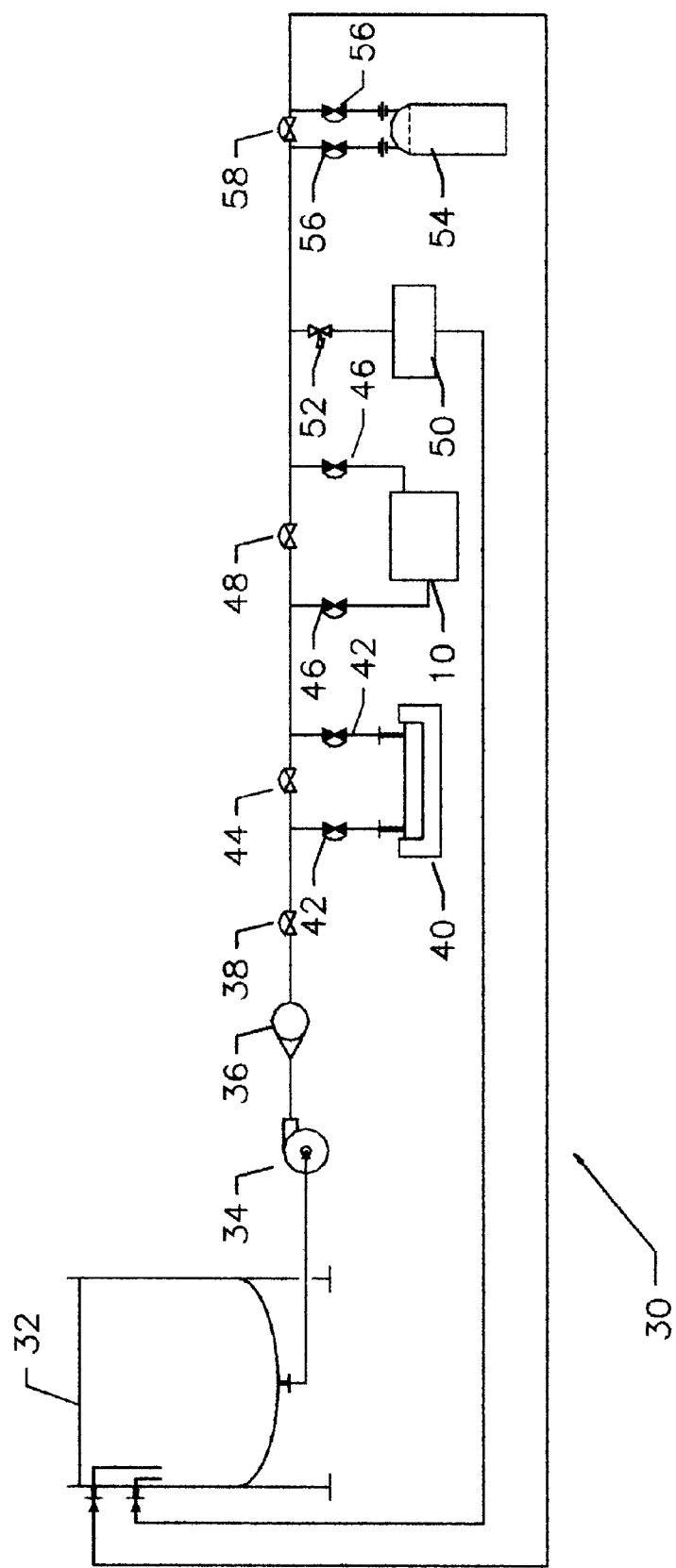
FIG. 2 is a schematic drawing of an experimental test system used to evaluate the performance of the present invention.

FIG. 2 is a schematic drawing of a laboratory water purification system 30 utilized in evaluating the present invention. The water system utilized for laboratory testing is configured to provide the flexibility required for a wide range of laboratory experiments. The exact volume of the water system is carefully measured. The feedwater for any experiment is added through the storage tank 32. Feedwater can range from typical point of use water to ultrapure water. An exact amount of organic impurities is also added through the storage tank. Since the water volume of the system is precisely known, the level of organics in an experiment can be mixed to a predetermined level and verified with the TOC Analyzer 50.

The system includes a pump 34, a flow meter (rotometer) 36, a throttling valve 38 to control system flow, an ultraviolet (UV) photolysing unit 40 with 185/254 nm UV lamps, a test chamber with a photocatalytic surface 10, a TOC Analyzer 50, and a mixed bed ion exchange (MBIX) unit 54. Valves 41 are provided to isolate (and bypass) the UV photolysing unit 40; Valves 46 isolate the photocatalytic reactor cell 10; and valves 56 isolate the MBIX unit. The TOC Analyzer 50 measures TOC, temperature, and resistivity. The water from the TOC analyzer is typically returned to the storage tank, but the sample stream can be diverted to drain from the TOC Analyzer if desired.

The system enables testing of variables including, but not limited to feedwater water quality (including analysis, conductivity, temperature), feedwater TOC, system flow rate, choice of applying either 185/254 nm or 254 nm UV energy, choice of applying the MBIX unit (including the choice of resins installed), a choice of the TOC analyzer utilized, the choice of the light source utilized to illuminate the photocatalytic surface (including wavelength, power, and the option to illuminate from multiple locations including 180 degrees), the choice to add microbubbles in the feedwater to the photocatalytic surface, and all of the possible choices and variations associated with the photocatalytic surface, including, but not limited to, material, surface preparation, surface coating, doping, size of pores, pore dispersion matrix, thickness of the ligaments, and the thickness of the photocatalytic surface.

EXAMPLES

Example 1

Figure 3:
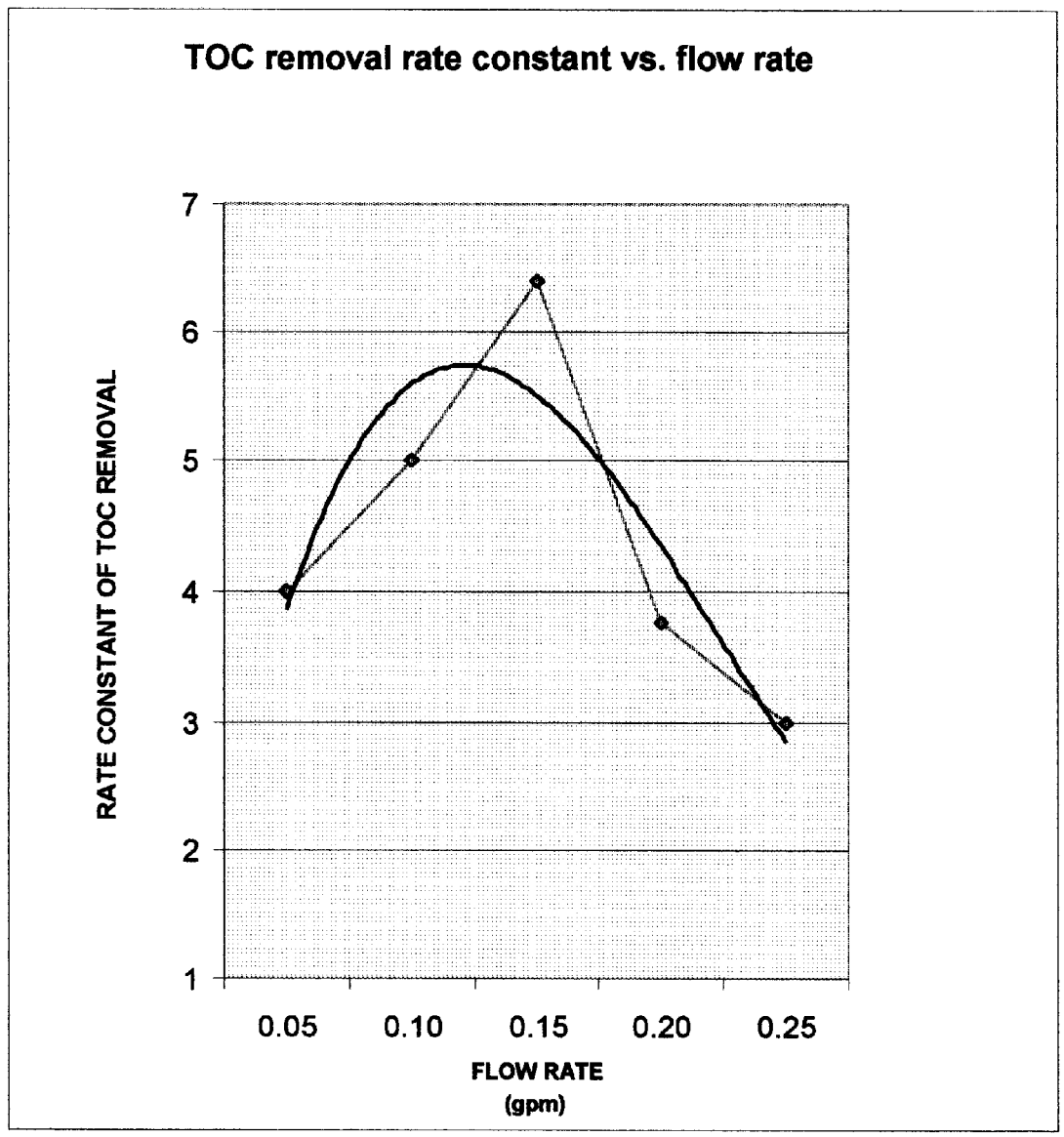
FIG. 3 shows the results of a flow rate optimization study.

FIG. 3 depicts TOC removal rate constants verses flow rate. Reticulated semiconductor unit (99.5% alumina, 80 ppi, 0.766 inches square by 0.25 inches thick) coated with $TiO_2$ in the anatase form was placed in the photocatalytic reactor of the test loop of FIG. 2. Acetic acid was spiked through the tank 32 and the flow was adjusted with valve 38 and monitored with flow meter 36. The photocatalytic substrate was illuminated with 365 nm light at 3 milliwatts/$cm^2$. The water was shunted past the ultraviolet (UV) photolysing unit 40 and MBIX unit 54 and passed through the photocatalytic reactor cell 10 which contains the reticulated semiconductor unit. The rate of oxidation of the acetic acid was monitored with a TOC analyzer 50 over time to establish rate constants for various surfaces and flows.

First order rates are compared among the different surfaces that have been tested to create a useful ranking of different surfaces and geometries. The higher the rate, the more effective is the surface. The first order rates are found to be significantly dependent on flow rates, which is related to the degree of turbulence and mixing that occurs. It is clear from FIG. 3. that peak effectiveness is found at around 0.15 gallons per minute in this particular cell and substrate arrangement.

Example 2

Figure 4:
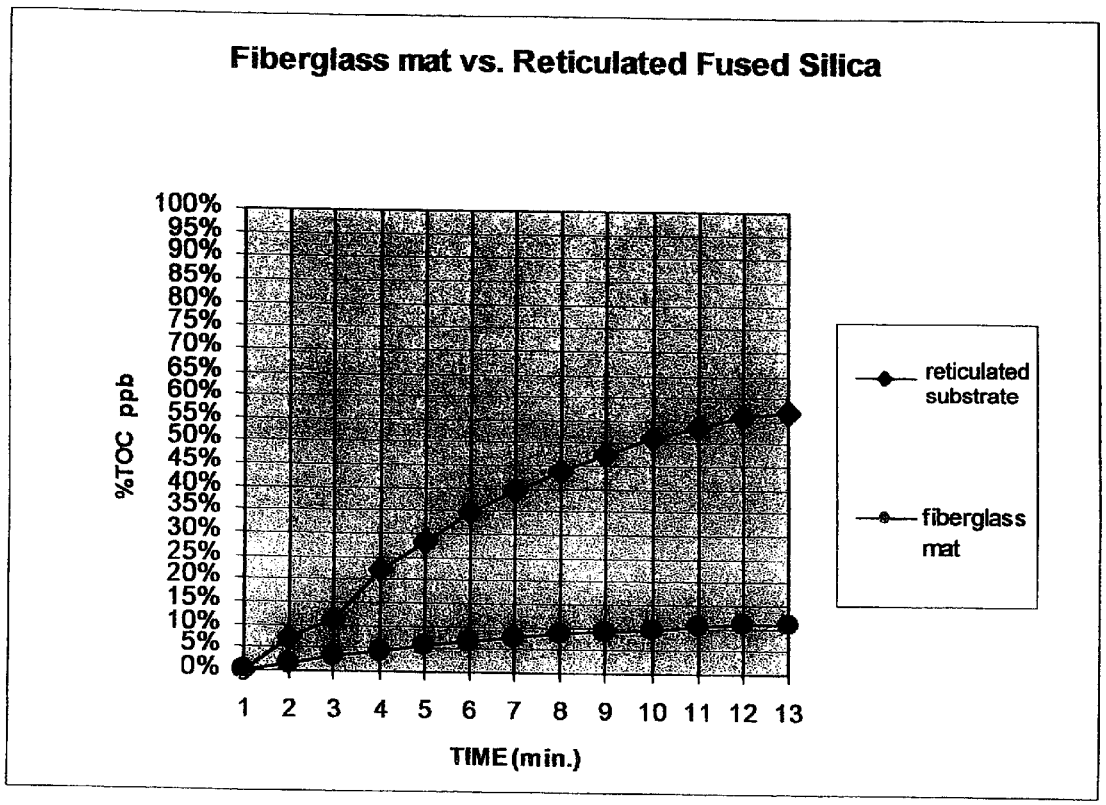
FIG. 4 shows the comparison of the photocatalytic destruction of acetic acid over time for a fiberglass mat substrate and a three dimensionally reticulated photocatalytic semiconductor unit utilized in an embodiment of the present invention.

FIG. 4 compares the performance of a prior art substrate and the reticulated semiconductor unit utilized in the present invention. It uses the same water loop configuration of FIG. 3. That is the water is shunted by the ultraviolet (UV) photolysing unit 40 and the MBIX unit 54. The photocatalytic surfaces compared are fused silica (22 ppi, 1.5 inches in diameter by 0.25 inches thick) and fiberglass mat. $TiO_2$ in the anatase form was deposited via sol gel techniques to the fused silica and the fiberglass mat. Both samples were platinum doped. Water was passed through the reticulated fused silica and fiberglass mat at 1 gallon per minute (gpm) and illuminated at 3 milliwatts/$cm^2$ at 365 nm wavelength. The water was spiked with 100 ppb acetic acid. The water was monitored with a TOC analyzer. Each photocatalytic semiconductor unit is independently evaluated according to the previously described procedures and the data was graphed. FIG. 4 compares the fiberglass mat substrate to the fused silica reticulated semiconductor unit. The reticulated fused silica underwent 57% mineralization in 13 minutes while fiberglass mat had 11% mineralization in 13 minutes. Turbulent flow of water through the reticulated semiconductor unit utilized in the present invention explains the better results. Even though the fiberglass mat is semitransparent to UV light and has more surface area than the reticulated photocatalytic semiconductor unit, it does not display turbulent mixing.

In "Guidelines for Ultrapure Water in Semiconductor Processing" (*Sematech Consortium, National Technology Roadmap for Semiconductors: Technology Needs*, 1997 Ed., p. 170) and the "Standard Guide for Ultrapure Water in the Electronics and Semiconductor Industry" (*ASTM Standard D5127–98, 'Standard Guide for Ultrapure Water Used in the Electronics and Semiconducto5 Industry, Vol.* 11.02). Water purity level is related to process line width. For line widths >0.5 microns total organic concentration (TOC) levels of <2.0 ppb are recommended. For line widths in the range 0.35–0.18 microns recommended TOC levels are below 1 ppb. Current technology struggles to achieve the 2 ppb level and has not come close to achieving the 1 ppb level. The International Road Map for Semiconductors shows the following schedule for achieving these water purity goals:

| Year: | 2000 | 2001 | 2002 | 2003 | 2004 | 2005 |
|---|---|---|---|---|---|---|
| Max. TOC Level: | 2 ppb | 2 ppb | 1 ppb | 1 ppb | <1 ppb | <1 ppb |

Current ultrapure water treatment systems utilize carbon and multimedia adsorption beds, various filtration units, reverse osmosis, and ion exchange membranes to remove inorganic contaminants and reduce TOC levels to the 10–20 ppb range. To bring TOCs down further, photolysing is used. This process requires deep UV irradiation (185 nm and 254 nm) using massed banks of UV lamps to decompose organics in water. The process is terribly inefficient, but is the only technology available to bring organic contamination down to marginally acceptable levels of 2–5 ppb. A common experience in the semiconductor industry is that at these levels, photolysing reaches a barrier at which point the curve of TOC versus total expended energy flattens out. This barrier, evidently, is due to one or more molecules present in low concentrations that are particularly difficult to destroy by photolysing.

Example 3

Figure 5:
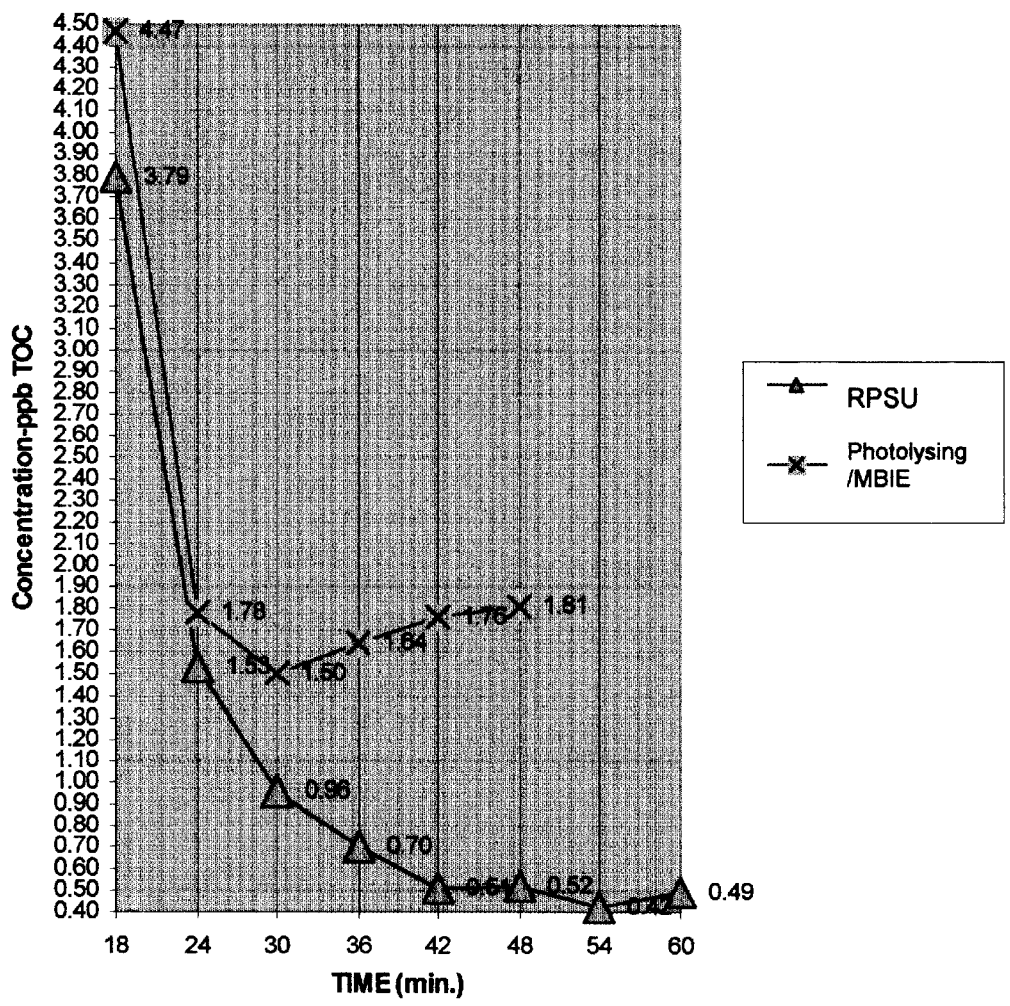
FIG. 5 shows a comparison of the photocatalytic destruction of acetic acid over time for UV photolysing/mixed bed ion exchange system compared to the reticulated semiconductor unit.

In FIG. 5 water in laboratory water purification system 30 of FIG. 2 was spiked with acetic acid (10 ppb) through tank 32 and passed through an ultraviolet (UV) photolysing unit 40 and then a test chamber with a photocatalytic surface 10 utilized in the present invention and then through the MBIX unit 54 and monitored with a TOC analyzer 50. The test chamber with a photocatalytic surface 10 was illuminated with a 365 nm (3 mW/cm2) light. The flow was 0.7 gpm.

FIG. 5 shows the results. First the destruction of acetic acid was evaluated with the ultraviolet (UV) photolysing unit 40 and the MBIX unit 54 in operation. Next the destruction of acetic acid was evaluated with the same configuration plus a test chamber with a photocatalytic surface 10 containing the reticulated semiconductor unit utilized in the present invention. With the ultraviolet (UV) photolysing unit 40 and the MBIX unit 54 in operation, the water reached a steady state barrier around 1.5 ppb TOC and then started to climb. While TOC in the water passing through the ultraviolet (UV) photolysing unit 40 and the MBIX unit 54 in operation plus the photocatalytic reticulated reactor with good light penetration, turbulent flow, and high surface area was reduced to 0.50 ppb.

We claim:

1. An apparatus for photocatalytic degradation of organic, inorganic, and microbiological contaminants in a fluid stream, said apparatus comprising:
   a reactor enclosure having a fluid inlet and a fluid outlet;
   at least one semiconductor unit, interposed between, and in fluid communication with, said fluid inlet and said fluid outlet, said semiconductor unit including a rigid, transparent or semi-transparent, three-dimensional substrate having a transparent or semi-transparent semiconductor photocatalytic surface with which the fluid stream comes into contact; and
   a light emitting device in optical proximity and communication to said at least one semiconductor unit, said light emitting device providing light having a wavelength of about 365 nm;
   wherein said light emitting device and said photocatalytic surface work cooperatively to remove contaminants from the fluid stream by photocatalytic reaction.

2. The apparatus of claim 1, wherein said photocatalytic surface and said substrate comprise the same material and are chemically integrated.

3. The apparatus of claim 1, wherein a photocatalytic material is incorporated into the substrate.

4. The apparatus of claim 1, wherein said photocatalytic surface comprises a layer of transparent material bonded to said substrate.

5. The apparatus as in either one of claim 3 or 4, wherein said photocatalytic material or said photocatalytic surface includes at least one doping material.

6. The apparatus of claim 5 wherein said at least one doping material is a transition metal.

7. The apparatus of claim 5 wherein said at least one doping material is selected from the group consisting of platinum, palladium, ruthenium, iridium, rhodium, silver, gold, copper, iron, cobalt, vanadium, niobium, tin, and zinc.

8. The apparatus of claim 5 wherein said doping material is vanadium pentoxide.

9. The apparatus of claim 8, wherein said vanadium pentoxide is included in an amount of about 7% by weight of the photocatalytic material.

10. The apparatus of claim 5, wherein the doping material is platinum.

11. The apparatus of claim 10, wherein said platinum is included in an amount of between about 0.05 and about 3% by weight of the photocatalytic material.

12. The apparatus of claim 4, wherein said photocatalytic surface is between about 1 and about 190 micrometers thick.

13. The apparatus of claim 1 wherein said photocatalytic surface is selected from the group consisting of $TiO_2$, ZnO, $CaTiO_3$, $SnO_2$, $MoO_3$, $Fe_2O_3$, and $WO_3$.

14. The apparatus of claim 1, wherein said photocatalytic surface is $TiO_2$.

15. The apparatus of claim 14, wherein said $TiO_2$ is in the anatase crystalline form having a grain size from approximately 1 to 30 nanometers.

16. An apparatus according to claim 14, wherein the $TiO_2$ is in the rutile crystalline form.

17. The apparatus of claim 1, wherein said substrate is a porous, open-cell, three dimensionally reticulated, fluid permeable structure.

18. The apparatus of claim 17 wherein said at least one semiconductor unit has a pore size ranging from about 10 to about 200 pores per square inch.

19. The apparatus of claim 17 wherein said at least one semiconductor unit has a pore size tapering from about 10 pores per square inch at the photocatalytic surface of said at least one semiconductor unit to about 200 pores per square inch toward the interior of said at least one semiconductor unit.

20. The apparatus of claim 1, wherein said substrate comprises a material selected from the group consisting of alumina, titania, silica, fused silica, glass, quartz, and organic polymers.

21. The apparatus of claim 1 wherein said at least one semiconductor unit is partially transparent to light having a wavelength between 180 nm and 700 nm.

22. The apparatus of claim 1 wherein said light emitting device is selected from the group consisting of light emitting diode, low pressure mercury lamp, medium pressure mercury lamp, high pressure mercury lamp and xenon lamp.

23. The apparatus of claim 1 further comprising light guides incorporated into said at least one semiconductor unit.

24. The apparatus of claim 23 wherein said light guides are selected from the group consisting of light fibers, quartz blocks, voids, gaps, microscopic gas bubbles, and separations.

25. An apparatus according to claim 1, wherein the substrate comprises glass.

26. A method of degrading organic, inorganic, and microbiological contaminants in a fluid stream by photocatalytic reaction, comprising:
   providing at least one semiconductor unit, wherein the semiconductor unit includes a rigid, transparent or semi-transparent, three-dimensional substrate having a transparent or semi-transparent semiconductor photocatalytic surface;
   providing a light emitting device in optical proximity to the photocatalytic surface; and
   directing the fluid stream over the photocatalytic surface whereby said contaminants are removed from said fluid stream by photocatalytic reaction in the presence of light having a wavelength of about 365 nm.

27. The method of claim 26, wherein the photocatalytic surface and the substrate comprise the same material and are chemically integrated.

28. The method of claim 26, wherein the substrate is a porous, open-cell, three dimensionally reticulated, fluid permeable structure.

29. The method of claim 28, wherein the semiconductor unit has a pore size ranging from about 10 to about 200 pores per square inch.

30. The method of claim 28, wherein the semiconductor unit has a pore size tapering from about 10 pores per square inch at the photocatalytic surface of said at least one semiconductor unit to about 200 pores per square inch toward the interior of said at least one semiconductor unit.

31. The method of claim 26, wherein a photocatalytic material is incorporated into the substrate.

32. The method of claim 26, wherein the photocatalytic surface comprises a layer of transparent material bonded to the substrate.

33. The method of claim 26, wherein the photocatalytic surface includes at least one doping material.

34. The method of claim 33 wherein the doping material is a transition metal.

35. The method of claim 33 wherein the doping material is selected from the group consisting of platinum, palladium, ruthenium, iridium, rhodium, silver, gold, copper, iron, cobalt, vanadium, niobium, tin, and zinc.

36. The method of claim 33 wherein the doping material is vanadium pentoxide.

37. The method of claim 33, wherein the doping material is platinum.

38. The method of claim 37, wherein the photocatalytic surface includes photocatalytic material and the platinum is included in an amount of between about 0.05 and about 3% by weight of the photocatalytic material.

39. The method of claim 26, wherein the photocatalytic surface is between about 1 and about 190 micrometers thick.

40. The method of claim 26 wherein the photocatalytic surface is selected from the group consisting of $TiO_2$, ZnO, $CaTiO_3$, $SnO_2$, $MoO_3$, $Fe_2O_3$, and $WO_3$.

41. The method of claim 40, wherein the photocatalytic surface is $TiO_2$ and is in the anatase crystalline form having a grain size from approximately 1 to 30 nanometers.

42. The method of claim 26, wherein the substrate comprises a material selected from the group consisting of alumina, titania, silica, fused silica, glass, quartz, and organic polymers.

43. The method of claim 26 wherein the light emitting device is selected from the group consisting of light emitting diode, low pressure mercury lamp, medium pressure mercury lamp, high pressure mercury lamp and xenon lamp.

44. A method according to claim 26, wherein, after removing said contaminants, the fluid stream has a total organic carbon content of less than 500 parts per trillion.

45. A method according to claim 26, wherein the fluid stream is water.

46. A method according to claim 26, wherein the fluid stream is from a water treatment system utilizing at least one of a carbon adsorption bed, reverse osmosis, an ion exchange membrane, or a filtration unit.

47. A method according to claim 26, further comprising photolysing the fluid stream prior to directing the fluid stream over the photocatalytic surface.

48. A method according to claim 26, wherein the substrate comprises glass.

49. A method according to claim 26, wherein said semiconductor unit comprises a plurality of substrates.

50. A method according to claim 49, comprising removing polar or non-polar contaminants.

51. A method according to claim 50, further comprising removing hydrophobic or hydrophilic contaminants.

52. A method according to claim 51, further comprising removing aromatic or aliphatic contaminants.

53. A method according to claim 52, further comprising removing alcoholic or acidic contaminants.

54. A method of purifying water, comprising:

contacting water from a manufacturing plant, said water containing at least one of organic, inorganic, and microbiological contaminants, with a semiconductor unit comprising a transparent or semi-transparent, three-dimensional substrate and a transparent or semi-transparent $TiO_2$ surface; and photocatalytically reacting said contaminants with light having a wavelength of about 365 nm, thereby removing said contaminants from the water to achieve a total organic carbon content of less than about 1 part per billion.

55. A method according to claim 54, wherein the plant is a semiconductor plant.

56. A method according to claim 54, wherein the plant is a pharmaceutical plant.

57. A method according to claim 54, wherein the plant is a power plant.

58. A method of purifying water, comprising:

contacting bottled water or water for a point of use application with a semiconductor unit comprising a transparent or semi-transparent, three-dimensional substrate and a transparent or semi-transparent $TiO_2$ surface, said water containing at least one of organic, inorganic, and microbiological contaminants; and photocatalytically reacting said contaminants with light having a wavelength of about 365 nm, thereby removing said contaminants from the water to achieve a total organic carbon content of less than about 1 part per billion.

* * * * *